(12) United States Patent
Terada

(10) Patent No.: US 8,632,758 B2
(45) Date of Patent: Jan. 21, 2014

(54) AQUEOUS HAIR CLEANSING AGENT

(75) Inventor: Eiji Terada, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/258,477

(22) PCT Filed: Mar. 26, 2010

(86) PCT No.: PCT/JP2010/002177
§ 371 (c)(1),
(2), (4) Date: Sep. 22, 2011

(87) PCT Pub. No.: WO2010/113446
PCT Pub. Date: Oct. 7, 2010

(65) Prior Publication Data
US 2012/0015894 A1 Jan. 19, 2012

(30) Foreign Application Priority Data
Mar. 31, 2009 (JP) .................. 2009-085836

(51) Int. Cl.
*A61Q 5/02* (2006.01)

(52) U.S. Cl.
USPC .............. 424/70.1; 424/70.22; 424/70.24; 514/18.8; 562/400

(58) Field of Classification Search
USPC ............ 424/70.1, 70.22, 70.24; 514/18.8; 562/400
See application file for complete search history.

(56) References Cited

U.S. PATENT DOCUMENTS

| 4,686,211 A * | 8/1987 | Hara et al. ............... 514/148 |
| 5,811,087 A | 9/1998 | Möhring et al. |
| 7,947,258 B2 | 5/2011 | Terada |
| 2006/0166845 A1 * | 7/2006 | Terada ..................... 510/127 |
| 2007/0224152 A1 | 9/2007 | Sakai et al. |
| 2007/0269397 A1 | 11/2007 | Terada |

FOREIGN PATENT DOCUMENTS

| CN | 101040825 A | 9/2007 |
| JP | 61-272295 | 12/1986 |
| JP | 2-175799 | 7/1990 |
| JP | 8-119828 | 5/1996 |
| JP | 9-110652 | 4/1997 |
| JP | 2000319136 A * | 11/2000 |
| JP | 2001-10934 | 1/2001 |
| JP | 2004123575 A * | 4/2004 |
| JP | 2006-1846 | 1/2006 |
| JP | 2007-1889 | 1/2007 |
| JP | 2007001889 A * | 1/2007 |
| JP | 2007-131583 | 5/2007 |
| JP | 2007-254355 | 10/2007 |
| JP | 2007-254356 | 10/2007 |

OTHER PUBLICATIONS

U.S. Appl. No. 13/258,246, filed Sep. 21, 2011, Terada.
International Search Report issued Jun. 29, 2010 in patent application No. PCT/JP2010/002177.
International Preliminary Report on Patentability and Written Opinion issued Nov. 15, 2011 in patent application No. PCT/JP2010/002177 filed Mar. 26, 2010.
U.S. Appl. No. 13/805,193, filed Dec. 18, 2012, Terada.
Office Action issued Feb. 17, 2013, in Chinese patent Application No. 201080013252.8 (w/English translation).
Combined Chinese Office Action and Search Report issued Sep. 28, 2012, in Patent Application No. 201080013252.8 (with English-language translation).

* cited by examiner

*Primary Examiner* — Ali Soroush
(74) *Attorney, Agent, or Firm* — Oblon, Spivak, McClelland, Maier & Neustadt, L.L.P.

(57) ABSTRACT

An aqueous hair cleansing agent contains a sulfate-type anionic surfactant having a specific structure, an ether carboxylate-type anionic surfactant having a specific structure, and an organic carboxylic acid or salt thereof, thereby has a pH of 1 to 5 at 25° C. when diluted 20-fold with water.

10 Claims, 2 Drawing Sheets

AQUEOUS HAIR CLEANSING AGENT

TECHNICAL FIELD

The present invention relates to an aqueous hair cleansing agent.

BACKGROUND ART

A principal purpose of a hair cleansing agent resides in removing dirt on hair and scalp, preventing dandruff and itchiness of the scalp, and keeping the hair and scalp clean. In view of obtaining a hair cleansing agent having high cleansing performance, it is preferable to use, as a main cleansing component, an anionic surfactant electrically charged at the equivalent level with the hair and scalp. It is more preferable to use a strong-acid-based anionic surfactant having a sulfuric acid group or sulfonic acid group in the anionic portion thereof, in view of preventing re-adsorption of dirt. Among others, an alkyl sulfate and alkyl ether sulfate are most generally used as the main component of a hair cleansing agent, by virtue of their rich foaming property and excellent cleansing performance.

The alkyl sulfate and alkyl ether sulfate, however, still have problems in terms of mildness to the scalp. Horny layer cells which form 10 to 20 layers in the surficial portion of the skin have important roles of keeping moisture within the skin, and protection from an external stimulation. The above-described alkyl sulfate and alkyl ether sulfate, however, permeate into the horny layer, strongly swell the cells, and elutes natural moisturizing components, such as an amino acid or lipid inherent to the cells, out from the cells. Accordingly, repetitive use of such hair cleansing agent, containing these surfactants as the main component, may tend to dry the skin due to the lowered moisture content of the scalp, and tend to induce itchiness of the scalp or provide a larger amount of dandruff because the surfactant and some stimulating substance may more readily permeate into the skin.

As low-stimulus cleansing bases, Patent Document 1 proposes an amino-acid-based surfactant such as an anionic surfactant in the form of alkyloylalkyl taurine salt, and Patent Document 2 proposes a weakly-acidic anionic surfactant such as polyoxyethylene alkyl ether carboxylate. The amino-acid-based surfactant and the polyoxyethylene alkyl ether carboxylate are less likely to swell the horny layer, and are mild to the skin. They, however, still have room for improvement as for basic performance of the cleansing agent, such as foamability and cleansing performance.

Patent Document 3 describes a technique of adding conditioning performance to a hair treatment composition. The document describes that a composition excellent in the conditioning performance may be obtained, without degrading the basic performances of the hair conditioner such as foamability and viscosity, by using a specific polyxoyalkylene alkenyl ether acetate.

RELATED DOCUMENT

Patent Document

[Patent Document 1] Japanese Patent Publication No. JP-A-S61-272295
[Patent Document 2] Japanese Patent Publication No. JP-A-H02-175799
[Patent Document 3] Japanese Patent Publication No. JP-A-2006-1846

DISCLOSURE OF THE INVENTION

According to the present invention, there is provided an aqueous hair cleansing agent which includes components (A), (B) and (C):

(A) a sulfate-type anionic surfactant represented by the following general formula (1):

$$R^1O(CH_2CH_2O)_nSO_3M \qquad (1)$$

wherein, in the general formula (1), $R^1$ represents an alkyl group or alkenyl group having 10 to 18 carbon atoms, M represents a cation derived from alkali metal, alkali earth metal, ammonium, alkanolamine or basic amino acid, and n represents a number from 0 to 5 estimated based on weight average;

(B) an ether carboxylate-type anionic surfactant represented by the following general formula (2) or (3):

$$R^2O(CH_2CH_2O)_mCH_2COOX \qquad (2)$$

$$R^2C(=O)NH(CH_2CH_2O)_mCH_2COOX \qquad (3)$$

wherein, in the general formulae (2) and (3), $R^2$ represents an alkyl group having 12 to 16 carbon atoms, X represents a cation derived from alkali metal, alkali earth metal, ammonium, alkanolamine or basic amino acid, and m represents a number of 0.5 to 10 estimated based on weight average; and (C) an organic carboxylic acid or salt thereof.

The aqueous hair cleansing agent has a pH of 1 to 5 at 25° C. when diluted 20-fold with water.

BRIEF DESCRIPTION OF THE DRAWINGS

The above and other objects, features and advantages of the present invention will be more apparent from the following description of certain preferred embodiments taken in conjunction with the accompanying drawings listed below.

DESCRIPTION OF THE EMBODIMENTS

Figure 1:
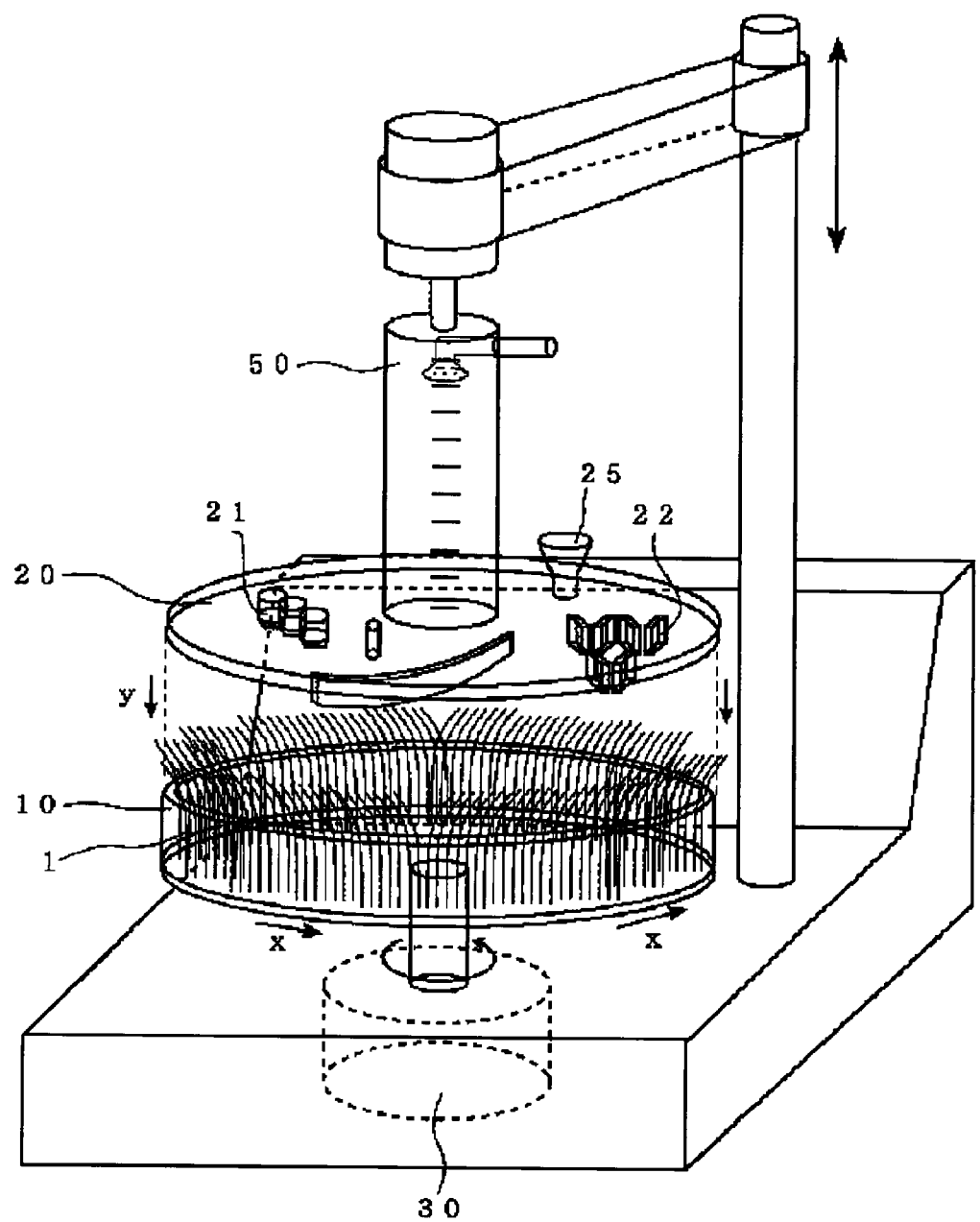
FIG. 1 is a schematic drawing illustrating a configuration of an apparatus used for evaluating quickness of foaming.

The present inventor investigated a hair cleansing agent which contains a sulfate-type anionic surfactant, more specifically alkyl sulfate or alkyl ether sulfate as a main cleansing component, aiming at improving mildness to the scalp, while keeping the basic performances of a cleansing agent. It was finally found that the technique described in Patent Document 3, previously mentioned in BACKGROUND ART, still has room for improvement in terms of a good balance between suppression of stimulation or itchiness of the scalp, and foamability.

From further investigations from the viewpoint of providing a hair cleansing agent, which is capable of ensuring rich foamability and reduced stimulation and itchiness of the scalp, the present inventor found that an aqueous hair cleansing agent excellent in foamability, which is a basic performance of a cleansing agent, suppressive to swelling of the horny layer of the skin, and less stimulus to the scalp, such as being less causative of itchiness, may be obtained by using a sulfate-type anionic surfactant, together with a specific alkyl ether carboxylate, and an organic carboxylic acid or salt thereof, and by adjusting the pH at 25° C. to 1 to 5 when diluted 20-fold by weight with water.

According to the present invention, an aqueous hair cleansing agent capable of ensuring rich foam, low stimulation and less itchiness to the scalp may be provided.

The aqueous hair cleansing agent of the present invention contains the components (A), (B) and (C) described below, and occasionally contains water. Note that all numerical ranges expressed using "to" in this specification are defined to include the upper and lower limits of the ranges. The individual components will specifically be explained.

(A) Sulfate-Type Anionic Surfactant Represented by the Following General Formula (1):

$$R^1O(CH_2CH_2O)_nSO_3M \quad (1)$$

(in the general formula (1), $R^1$ represents an alkyl group or alkenyl group having 10 to 18 carbon atoms, M represents a cation derived from alkali metal, alkali earth metal, ammonium, alkanolamine or basic amino acid, and n represents a number from 0 to 5 estimated based on weight average.)

(B) Ether Carboxylate-Type Anionic Surfactant Represented by the Following General Formula (2) or (3):

$$R^2O(CH_2CH_2O)_mCH_2COOX \quad (2)$$

$$R^2C(=O)NH(CH_2CH_2O)_mCH_2COOX \quad (3)$$

(in the general formulae (2) and (3), $R^2$ represents an alkyl group having 12 to 16 carbon atoms, X represents a cation derived from alkali metal, alkali earth metal, ammonium, alkanolamine or basic amino acid, and m represents a number from 0.5 to 10 estimated based on weight average.)

First, the component (A) will be explained.

In the aqueous hair cleansing agent of the present invention, the component (A) is a sulfate-type anionic surfactant, and more specifically, an alkyl sulfate or alkyl ether sulfate represented by the general formula (1) in the above.

From the viewpoint of stably obtaining rich foam, it is preferable for the general formula (1) to assume $R^1$ having 12 to 14 carbon atoms, 1 to 2 estimated based on weight average for n, and ammonium or sodium for M.

Among these, in view of ensuring quick foaming and excellent cleansing performance, polyoxyethylene alkyl ether sulfate having an alkyl group of 12 to 14 carbon atoms for $R^1$, 1 to 2 for n estimated based on weight average, and ammonium or sodium for M in the general formula (1), is preferable.

The component (A) may be a single species, or may be a combination of two or more species. In view of further improving the foamability, the content of component (A) may be adjusted typically to 1% by weight or more of the total aqueous hair cleansing agent, preferably 5% by weight or more, and more preferably 8% by weight or more. From another viewpoint of low dermal stimulation, the content of component (A) relative to the total aqueous hair cleansing agent may be adjusted typically to 25% by weight or less, preferably 23% by weight or less, and more preferably 20% by weight or less.

From still another viewpoint of ensuring a good balance among rich foam, pH during use, and finger combability during rinsing, the content is preferably 1 to 25% by weight relative to the total aqueous hair cleansing agent of the present invention, more preferably 5 to 23% by weight, and even more preferably 8 to 20% by weight.

Next, the component (B) will be explained.

In the aqueous hair cleansing agent of the present invention, the ether carboxylate-type anionic surfactant composing the component (B) means a group of compounds each having a hydrophobic group and a carboxyl group bound via a polyoxyethylene chain placed in between, and therefore includes alkyl ether carboxylate and alkylamide ether carboxylate, which are represented by the general formulae (2) and (3) in the above, respectively.

In view of further improving a balance between foamability and suppression of swelling of the horny layer, $R^2$ in the formulae (2) and (3) is preferably an alkyl group having 12 to 16 carbon atoms, and more preferably an alkyl group having 12 carbon atoms.

In the general formulae (2) and (3), while an average molar number m of addition of ethylene oxide is 0.5 to 10, it is preferably 1 to 6 from the view point of foamability.

The counter ion X in the general formula (2) and (3) may be exemplified by alkali metal such as sodium and potassium; alkali earth metal such as calcium and magnesium; ammonium;
ammonium derived from alkanolamine such as monoethanolamine, diethanolamine, and triethanolamine; and
cation derived from basic amino acid such as arginine and lysine.

From the viewpoints of foamability and effect of suppressing swelling of the horny layer, the component represented by the general formula (2) in the above is preferable as the component (B).

The component (B) may be a single species, or may be a combination of two or more species.

From the viewpoint of suppressing swelling of the horny layer, content of the component (B) may typically be 0.5% by weight or more of the total aqueous hair cleansing agent, preferably 1% by weight or more, and more preferably 2% by weight or more. In view of further improving the foamability, the content of the component (B) relative to the total aqueous hair cleansing agent may be adjusted typically to 10% by weight or less, preferably 8% by weight or less, and more preferably 6% by weight or less.

In view of further improving a balance among suppression of swelling of the horny layer, rich foam, and finger combability during rinsing, the content of component (B) relative to the total aqueous hair cleansing agent of the present invention is preferably 0.5 to 10% by weight, more preferably 1 to 8% by weight, and even more preferably 2 to 6% by weight.

From the viewpoint of excellent foamability, the components (A) and (B) preferably give the weight ratio of the component (B) relative to the total of the components (A) and (B) (i.e. (B)/((A)+(B))) of from, of 50% or less, more preferably 40% or less, and even more preferably 30% or less. From another viewpoint of mildness to the scalp, the weight ratio given by $(B)/((A)+(B))\times 100(\%)$ may typically be 5% or larger, and preferably 10% or larger.

While the reason why the balance between foamability during cleansing and low stimulation to the scalp is improved, as a result of inclusion of the component (A) and the component (B) as essential components, is not exactly clear, it is supposedly because the component (B) properly adsorbs onto the surface of the horny layer of the scalp to thereby form a protective film, and effectively suppresses swelling of the horny layer, while function of the component (A) is kept unchanged.

The aqueous hair cleansing agent of the present invention further contains one or more species of organic carboxylic acid or salt thereof which composes the component (C). The component (C) will be explained below.

In the aqueous hair cleansing agent of the present invention, the organic carboxylic acid composing the component (C) preferably has 2 to 6 carbon atoms, and is more preferably dicarboxylic acid (which may have hydroxy groups) or hydroxymonocarboxylic acid. More specifically, the dicarboxylic acid may be exemplified by malonic acid, succinic acid, glutaric acid, adipic acid, maleic acid, fumaric acid, phthalic acid, and oxalic acid. The dicarboxylic acid having hydroxy groups may be exemplified by malic acid and tartaric acid. The hydroxymonocarboxylic acid may be exemplified by glycolic acid, lactic acid, hydroxyacrylic acid, oxybutyric acid, glyceric acid, and gluconic acid. Among these organic carboxylic acids, preferable examples include glycolic acid, lactic acid, malonic acid, maleic acid, and malic acid. Salts of these organic carboxylic acids may be exemplified by those formed with alkali metal, alkali earth metal, ammonia, and organic amine compound.

The component (C) may be a single species, or may be a combination of two or more species, wherein the content of which is preferably 0.1 to 5% by weight, more preferably 0.2 to 3% by weight, and even more preferably 0.5 to 2% by weight of the aqueous hair cleansing agent, in view of ensuring a sufficient level of scalp improvement.

Next, pH of the aqueous hair cleansing agent of the present invention will be explained.

In view of maximizing the effect of improving scalp conditions by the organic carboxylic acid composing the component (C), the aqueous hair cleansing agent of the present invention, containing such component (C), preferably has a pH value of 2 to 4.5, and more preferably 3 to 4.5, at 25° C. when diluted 20-fold by weight with water.

From another viewpoint of maximizing the effect of suppressing swelling of the horny layer by the ether carboxylate-type anionic surfactant composing the component (B), the aqueous hair cleansing agent of the present invention preferably has a pH value of 1 to 5, more preferably 2 to 4.5, and even more preferably 3 to 4.5, at 25° C. when diluted 20-fold by weight with water.

Since the ether carboxylate composing the component (B) is a weak acid, it exists in a form of acid (undissociated form) under low pH, whereas it exists in a form of anion (dissociated form) under high pH. More specifically, most of the ether carboxylate exists in a form of acid at 25° C. under pH 1 to 5 when diluted 20-fold with water, and is particularly effective for suppressing swelling of the horny layer.

In addition, the dandruff suppressive effect may more effectively be expressed under pH 1 to 5, by virtue of its anti-bacterial effect against resident bacteria. Accordingly, the aqueous hair cleansing agent of the present invention typically has excellent foamability and anti-dandruff performance, and is also capable of suppressing itchiness of the scalp as a result of suppression of swelling of the horny layer.

For the purpose of adjusting pH to 1 to 5 in the present invention, inorganic or organic acid, or alkali agent may be used while being appropriately combined and quantified.

Of these, the inorganic acid may be exemplified by hydrochloric acid, sulfuric acid, and phosphoric acid.

The organic acid may be exemplified by citric acid and glutamic acid, besides the above-described organic carboxylic acid. In the present invention, an additional effect of preventing dandruff and itchiness may be obtained, particularly by using one or more species of organic carboxylic acid or salt thereof, which composes the component (C).

An aqueous hair cleansing agent which is further well balanced among foamability, anti-dandruff performance, and low stimulation, and also excellent in stability in manufacturing, may be obtained by using the alkyl sulfate or alkyl ether sulfate represented by the general formula (1), that is the component (A), as the base, together with the alkylether carboxylate composing the component (B), and the organic acid salt composing the component (C), and by adjusting pH at 25° C. to 1 to 5 when diluted 20-fold with water.

The aqueous hair cleansing agent of the present invention may also reduce volume of water for rinsing, since the surfactant contained therein is less likely to remain on the hair or scalp.

The aqueous hair cleansing agent of the present invention may further be configured to contain at least one species of an anti-inflammatory agent.

Examples of the anti-inflammatory agent includes glycyrrhetinic acid, glycyrrhizic acid and derivatives thereof; and also include components having an anti-inflammatory function, such as E-aminocaproic acid, allantoin, sodium guaiazulene sulfonate, d-camphor, l-menthol, urea, pyridoxine dipalmitate, glycyrrhetinyl stearate, tranexamic acid, vitamin A oil, hydrocortisone, prednisolone, pyridoxine hydrochloride, Kankohso (photosensitizer) 301, zinc oxide, and hydrocortisone acetate. The derivatives of glycyrrhetinic acid or glycyrrhizic acid include salts which include alkali metal salts represented by sodium salt and potassium salt, and ammonium salt; and esters such as glycerin ester and stearyl ester. More specifically, dipotassium glycyrrhizinate, disodium glycyrrhizinate, trisodium glycyrrhizinate, monoammonium glycyrrhizinate, glycerin glycyrrhetinate, and stearyl glycyrrhetinate may be exemplified.

The anti-inflammatory agent may be a single species, or may be a combination of two or more species, wherein the content of which is preferably 0.001 to 10% by weight, more preferably 0.005 to 5% by weight, and even more preferably 0.01 to 1% by weight.

In view of further improving the cleansing performance, the aqueous hair cleansing agent of the present invention may contain a nonionic surfactant or amphoteric surfactant.

The nonionic surfactant adoptable herein may be exemplified by polyoxyalkylene solbitan fatty acid ester, polyoxyalkylene solbit fatty acid ester, polyoxyalkylene glycerin fatty acid ester, polyoxyalkylene fatty acid ester, polyoxyalkylene alkyl ether, polyoxyalkylene alkylphenyl ether, polyoxyalkylene (hydrogenated) castor oil, sucrose fatty acid ester, polyglycerin alkyl ether, polyglycerin fatty acid ester, fatty acid alkanolamide, alkylglycoside, mono alkyl and monoalkenyl glyceryl ether.

Among these, polyoxyalkylene solbitan fatty acid ester such as polyoxyethylene solbitan fatty acid ester, polyoxyalkylene fatty acid ester such as polyoxyalkylene ($C_8$ to $C_{20}$) fatty acid ester, and polyoxyalkylene (hydrogenated) castor oil such as polyoxyethylene hydrogenated castor oil, and alkylglycoside are preferable.

Also fatty acid alkanolamide is a preferable nonionic surfactant, allowing either monoalkanolamide or dialkanolamide. Those having an acyl group of 8 to 18 carbon atoms, in particular 10 to 16 carbon atoms are preferable. Also those having a hydroxyalkyl group of 2 to 3 carbon atoms are preferable, which are exemplified by oleic acid diethanolamide, palm kernel oil fatty acid diethanolamide, coconut oil fatty acid diethanolamide, lauric acid diethanolamide, polyoxyethylene coconut oil fatty acid monoethanolamide, coconut oil fatty acid monoethanolamide, lauric acid isopropanolamide, and lauric acid monoethanolamide.

Also glyceryl monoalkyl ether or glyceryl monoalkenyl ether is a preferable nonionic surfactant, where the alkyl group or alkenyl group is preferably a straight-chain or branched alkyl group having 4 to 10 carbon atoms, in particular 8 to 10 carbon atoms. The specific examples include n-butyl group, isobutyl group, n-pentyl group, 2-methylbutyl group, isopentyl group, n-hexyl group, isohexyl group, n-heptyl group, n-octyl group, 2-ethylhexyl group, n-decyl group, and isodecyl group. In particular, 2-ethylhexyl group and isodecyl group are preferable.

The amphoteric surfactant may be exemplified by betaine-based surfactants. Among these, alkyl dimethyl aminoacetic acid betaine, fatty acid amidopropyl betaine, and alkyl hydroxy sulfobetaine are more preferable, wherein fatty acid amidopropyl betaine is more preferable. The fatty acid amidopropyl betaine preferably has an acyl group of 8 to 18 carbon atoms, in particular 10 to 16 carbon atoms, wherein more preferable examples include lauric acid amidopropyl betaine, palm kernel oil fatty acid amidopropyl betaine, and coconut oil fatty acid amidopropyl betaine.

Each of these surfactants may be a single species, or may be a combination of two or more species contained in the aqueous hair cleansing agent. In view of obtaining the aqueous hair cleansing agent of the present invention in the form of a water-based liquid cleaner, it is preferable to use fatty acid amidopropyl betaine, fatty acid alkanolamide, or mono alkylglyceryl ether, together with the components (A), (B), not only because the foamability is improved, but also because the appropriate level of pH may be obtained.

The content of these surfactant is preferably 0.1 to 15% by weight in the hair cleansing agent of the present invention, in view of obtaining a good effect of enhancing the foamability. From this point of view, the content is more preferably 0.5 to 8% by weight, and even more preferably 1 to 6% by weight.

The aqueous hair cleansing agent of the present invention may further contain a cationic surfactant, cationized polymer or silicones, for the purpose of improving the finger combability during rinsing, and of improving styling of hair after being dried.

The cationic surfactant may be exemplified by alkyltrimethyl ammonium salt, alkoxy trimethyl ammonium salt, dialkyldimethyl ammonium salt, alkyldimethylamine salt, alkoxy dimethylamine salt, and alkylamide dimethylamine salt.

(i) Alkyl Trimethylammonium Salt

This is exemplified by those represented by the following general formula:

$$R^4—N^+(CH_3)_3Q^-$$

(in the general formula, $R^4$ represents an alkyl group having 12 to 22 carbon atoms, and $Q^-$ represents a halogen (chlorine or bromine) ion.)

More specifically, cetyl trimethylammonium chloride, stearyl trimethylammonium chloride, and behenyl trimethylammonium chloride may be exemplified.

(ii) Alkoxy Trimethylammonium Salt

This is exemplified by those represented by the following general formula:

$$R^5—O—R^6—N(CH_3)_3Q^-$$

(in the formula, $R^5$ represents an alkyl group having 12 to 22 carbon atoms, $R^6$ represents an ethylene group or propylene group, and $Q^-$ is same as described in the above.)

More specifically, stearoxypropyl trimethylammonium chloride, stearoxyethyl trimethylammonium chloride, and stearoxyhydroxypropyl trimethylammonium chloride may be exemplified.

(iii) Dialkyldimethyl Ammonium Salt

This is exemplified by those represented by the following general formula:

$$R^7_2—N^+(CH_3)_2Q^-$$

(in the general formula, $R^7$ represents an alkyl group having 12 to 22 carbon atoms or benzyl group, and $Q^-$ is same as described in the above.)

More specifically, distearyl dimethyl ammonium chloride may be exemplified.

(iv) Alkyldimethylamine Salt

This is exemplified by those represented by the following general formula:

$$R^8—N(CH_3)_2$$

(in the general formula, $R^8$ represents an alkyl group having 12 to 22 carbon atoms.)

More specifically, organic acid salts of behenyl dimethylamine and stearyl dimethylamine may be exemplified.

(v) Alkoxydimethylamine Salt

This is exemplified by those represented by the following general formula:

$$R^9—O—R^{10}—N(CH_3)_2$$

(in the general formula, $R^9$ represents an alkyl group having 12 to 22 carbon atoms, and $R^{10}$ represents an ethylene group or propylene group.)

(vi) Alkylamide Dimethylamine Salt

This is exemplified by those represented by the following general formula:

$$R^{11}—C(=O)NH—R^{12}—N(CH_3)_2$$

(in the general formula, $R^{11}$ represents an alkyl group having 11 to 21 carbon atoms, and $R^{12}$ represents an ethylene group or propylene group.)

Cationic surfactants other than the above-described (i) to (vi) may be exemplified by lanolin fatty acid aminopropylethyldimethyl ammonium ethyl sulfate, lanolin fatty acid aminoethyltriethylammonium ethyl sulfate, lanolin fatty acid aminopropyltriethylammonium ethyl sulfate, lanolin fatty acid aminoethyltrimethylammonium methyl sulfate, lanolin fatty acid aminopropylethyldimethylammonium methyl sulfate, isoalkanoic acid ($C_{14}$ to $C_{20}$) aminopropylethyldimethylammonium ethyl sulfate, isoalkanoic acid ($C_{18}$ to $C_{22}$) aminopropylethyldimethylammonium ethyl sulfate, isostearic acid aminopropylethyldimethylammonium ethyl sulfate, isononanoic acid aminopropylethyldimethylammonium ethyl sulfate and alkyltrimethylammonium saccharin.

Two or more species of the cationic surfactant may be combined, wherein the content of which is preferably 0.01 to 10% by weight of the aqueous hair cleansing agent of the present invention, more preferably 0.05 to 5% by weight, and even more preferably 0.1 to 2% by weight, in view of smoothness over a period from washing to rinsing.

Next, the cationized polymer may be exemplified by cationized cellulose, cationized starch, cationized fenugreek gum, cationized guar gum, cationized tara gum, cationized locust bean gum, cationized xanthan gum, diallyldialkylammonium salt/acrylamide copolymer, vinylimidazolium trichloride/vinylpyrrolidone copolymer, hydroxyethylcellulose/dimethyldiallyl ammonium chloride copolymer, vinylpyrrolidone/quaternized dimethylaminoethyl methacrylate copolymer, polyvinylpyrrolidone/alkylamino acrylate copolymer, polyvinylpyrrolidone/alkylamino acrylate/vinylcaprolactam copolymer, vinylpyrrolidone/methacrylamidopropyl trimethylammonium chloride copolymer, alkylacrylamide/acrylate/alkylamino alkylacrylamide/polyethylene glycol methacrylate copolymer, adipic acid/dimethylaminohydroxypropylethylene triamine copolymer (Cartaretine from Sandoz US), and cationic polymers disclosed in Japanese Patent Publication Nos. JP-A-S53-139734 and JP-A-S60-36407. In particular, cationized cellulose, cationized fenugreek gum, cationized guar gum, cationized tara gum, cationized locust bean gum, and diallyldialkylammonium salt/acrylamide copolymer are preferable.

The cationized polymer are also commercially available under trade names of MERQUAT® 550 (from NALCO Company, copolymer of acrylamide and diallyl dimethyl ammonium salt; CTFA name=Polyquaternium-7), LUVIQUAT® FC370 (from BASF Corporation, copolymer of 1-vinyl-2-pyrrolidone and 1-vinyl-3-methylimidazolium salt; CTFA name=Polyquaternium-16), GAFQUAT® 755N (from ISP, Inc., copolymer of 1-vinyl-2-pyrrolidone and dimethylaminoethyl methacrylate; CTFA name=Polyquaternium-11), UCARE® polymer JR and Ucar polymer LR Series (from Amerchol Corporation, salts of reaction product between trimethylammonium-substituted epoxide and hydroxyethylcellulose; CTFA name=Polyquaternium-10), POIZ® C-60H, POIZ® C-80M, POIZ® C-150L (from Kao Corporation, salts of reaction product between trimethylammonium-substituted epoxide and hydroxyethylcellulose; CTFA name=Polyquaternium-10), JAGUAR® Series (from Rhodia, salt of reaction product between trimethylammonium-substituted epoxide and guar gum), CANTINAL® CF-100 (from TOHO Chemical Industry Co., Ltd., salt of reaction product between trimethylammonium-substituted epoxide and fenugreek gum), CANTINAL® CTR-100 (from TOHO Chemical Industry Co., Ltd., salt of reaction product between trimethylammonium-substituted epoxide and tara gum), and CANTINAL® CLB-100 (from TOHO Chemical Industry Co., Ltd., salt of reaction product between trimethylammonium-substituted epoxide and locust bean gum).

Two or more species of these cationized polymers may be combined, wherein the content of which is preferably 0.01 to 3% by weight of the aqueous hair cleansing agent of the present invention, more preferably 0.05 to 2% by weight, and even more preferably 0.1 to 1% by weight, in view of smoothness over a period from washing to rinsing.

The silicones may be exemplified by (I) to (III) listed below.

(I) Dimethylpolysiloxane

This is exemplified by those represented by the following general formula (4):

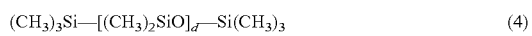

$(CH_3)_3Si-[(CH_3)_2SiO]_d-Si(CH_3)_3$     (4)

(in the general formula (4), d represents a number of 3 to 20,000.)

The dimethylpolysiloxane exist as dispersed particles in the aqueous hair cleansing agent, wherein average particle size of the dispersed particles is preferably 0.1 to 100 μm, more preferably 0.1 to 50 μm, even more preferably 0.1 to 4 μm, and even more preferably 0.1 to 2 μm, in view of excellence of finishing after drying, and storage stability of the hair cleansing agent.

The average particle size of the polydimethylsiloxane emulsion herein means the median diameter measured by laser light scattering method, and may be measured using a general particle analyzer based on laser light scattering, such as LS-130 from Coulter Corporation.

This sort of dimethylpolysiloxane adoptable herein is commercially available under the name of "Silicone CF2450" from Dow Corning Toray Co., Ltd. which contains 60% by weight of dimethylpolysiloxane oil represented by the general formula (4) with d=300 to 6,500, and has an average particle size of 0.8 μm; or under the name of "Silicone CF2460" from Dow Corning Toray Co., Ltd., which contains 75% by weight of dimethylpolysiloxane oil with d=300 to 6,500, and has an average particle size of 20 μm.

The dimethylpolysiloxane is preferably contained in an amount of from 0.01 to 10% by weight of the aqueous hair cleansing agent of the present invention, preferably 0.05 to 6% by weight, more preferably 0.3 to 3% by weight, and even more preferably 0.5 to 2% by weight, in view of improving foam texture, and touch or gloss of hair after being dried.

(II) Amino-Modified Silicone

While various amino-modified silicones may be adoptable, a product listed under the name of Amodimethicone in CTFA Dictionary (Cosmetic Ingredient Dictionary, USA), 9th Edition, 2002, Volume 1, p. 107, having an average molecular weight of approximately 3000 to 100,000, is preferable. The commercially available products may be exemplified by SM 8704C (from Dow Corning Toray Co., Ltd.), DC 929 (from Dow Corning Corporation), KT 1989 (from Momentive Performance Materials Inc.), 8500 Conditioning Agent, DOW CORNING TORAY SS-3588, and DOW CORNING TORAY SILSTYLE 104 (from Dow Corning Toray Co., Ltd.).

(III) Other Silicones

Other silicones besides those described above may be exemplified by polyether-modified silicone, methylphenyl polysiloxane, aliphatic acid-modified silicone, alcohol-modified silicone, alkoxy-modified silicone, epoxy-modified silicone, fluorine-modified silicone, cyclic silicone, and alkyl-modified silicone.

Two or more species of these amino-modified silicone and other silicones may be combined, wherein the content of which is preferably 0.01 to 5% by weight of the aqueous hair cleansing agent of the present invention, more preferably 0.05 to 2% by weight, and even more preferably 0.1 to 1% by weight, in view of smoothness over a period from washing to rinsing.

The aqueous hair cleansing agent of the present invention may further contain a pearlescent agent containing ethylene glycol monofatty acid ester, ethylene glycol difatty acid ester, ethylene glycol mono alkyl ether or ethylene glycol dialkyl ether.

The ethylene glycol monofatty acid ester may be exemplified by ethylene glycol monostearate and ethylene glycol monobehenate, and the ethylene glycol difatty acid ester may be exemplified by ethylene glycol distearate and ethylene glycol dibehenate. The ethylene glycol mono alkyl ether may be exemplified by ethylene glycol monostearyl ether, and the ethylene glycol dialkyl ether may be exemplified by ethylene glycol distearyl ether.

Each of them may be a combination of two or more species, wherein the content of which is preferably 0.1 to 10% by weight of the aqueous hair cleansing agent of the present invention, more preferably 0.5 to 5% by weight, and even more preferably 1 to 4% by weight, in view of improving storage stability, smoothness during foaming and rinsing, and stability of the hair cleansing agent.

The aqueous hair cleansing agent of the present invention may contain an oil component as another conditioning agent. The oil component may be exemplified by hydrocarbon oils such as squalene, squalane, liquid paraffin, liquid isoparaffin, and cycloparaffin;

glycerides such as castor oil, cacao oil, mink oil, avocado oil, olive oil, sunflower oil, and camellia oil;

waxes such as beeswax, spermaceti, lanolin, and carnauba wax;

higher alcohols such as cetyl alcohol, oleyl alcohol, stearyl alcohol, isostearyl alcohol, 2-octyl dodecanol, myristyl alcohol, behenyl alcohol, and cetostearyl alcohol;

ester oils such as isopropyl palmitate, isopropyl myristate, octyldodecyl myristate, hexyl laurate, cetyl lactate, propylene glycol monostearate, oleyl oleate, hexadecyl 2-ethylhexanoate, isononyl isononanoate, and tridecyl isononanoate;

higher fatty acids such as capric acid, lauric acid, myristic acid, palmitic acid, stearic acid, behenic acid, oleic acid, coconut oil fatty acid, isostearic acid, and isopalmitic acid; and other materials such as isostearyl glyceryl ether, and poly (oxypropylene)butyl ether. Among these, higher fatty acids, higher alcohol, and glyceride are preferable, and lauric acid, myristyl alcohol, cetyl alcohol, stearyl alcohol, sunflower oil, and camellia oil are more preferable. These oil components may be a single species, or may be a combination of two or more species, wherein the content of which is preferably 0.1 to 2% by weight of the aqueous hair cleansing agent of the present invention, more preferably 0.2 to 1.5% by weight, and even more preferably 0.3 to 1% by weight.

The aqueous hair cleansing agent of the present invention may contain a viscosity adjusting agent. The viscosity adjusting agent may be exemplified by hydroxyethylcellulose, methylcellulose, polyethylene glycol, polypropylene glycol, ethylene glycol, propylene glycol, isoprene glycol, ethanol, glycerin, benzyl alcohol, benzyloxy ethanol, phenoxy ethanol, and clay minerals, salts (sodium chloride, ammonium chloride, sodium citrate, and so forth), among which benzyl alcohol, ethanol, polypropylene glycol, sodium chloride, and sodium citrate are preferable. The viscosity adjusting agent may be a single species, or may be a combination of two or more species, wherein the content of which is preferably 0.01 to 5% by weight of the aqueous hair cleansing agent of the present invention, more preferably 0.05 to 4% by weight, and even more preferably 0.1 to 3% by weight, in view of richness and quality of foam.

Besides the above-described components, any components adopted to a general hair cleansing agent may appropriately be added to the aqueous hair cleansing agent of the present invention, depending on the need. The components may be exemplified by antiseptic agent; chelating agent; moisturizers such as sorbitol and panthenol; colorants such as dye and pigment; extracts such as polar solvent extract of eucalyptus, protein obtained from shell having a nacreous layer or from pearl, or hydrolysate thereof, honey, royal jelly, silk-derived protein or hydrolysate thereof, protein-containing extract obtained from leguminous plant seed, *Panax ginseng* extract, rice germ extract, bladderwrack extract, aloe extract, Alpinia leaf extract, and chlorella extract; pearl pigment such as mica-titanium; perfume; UV absorber; antioxidant; and other components listed in Encyclopedia of Shampoo Ingredients (written by Anthony L. L. Hunting, 1983, published by Micelle Press)).

While the existing form of the aqueous hair cleansing agent of the present invention may appropriately be selectable from liquid, gel and so forth, it is preferable to use water or lower alcohol, and particularly water, as a medium.

EXAMPLES

Examples 1 to 7 and Comparative Examples 1 to 8

Aqueous hair cleansing agents listed in Table 1 were prepared, and evaluated by the methods described below. Results are shown in Table 1. Note that the pH values herein were measured at 25° C. after 20-fold dilution with water.
Methods of Evaluation
(1) Quickness of Foaming Quickness of foaming was evaluated using the method and the apparatus described in Japanese Patent Publication No. JP-A-H10-73584.

More specifically, FIG. 1 illustrates an apparatus for evaluating foamability, having a container 10 for housing an article to be applied with the cleansing agent (hair 1), projections 21, 22 which are brought into contact with the hair 1, a gauge 50 for measuring foam produced in the container 10, a lid 20 which covers the container 10, and guides the foam produced in the container 10 towards the gauge 50, and a motor 30 for moving the container 10 so as to bring the hair 1 housed in the container 10 and the projections 21, 22 into sliding contact. The hair 1 was wet with an equal volume of water, 1.5 mL of each sample to be evaluated and 0.3 mL of model sebum composed of lanolin were injected through an injection port 25, and the amount of foam was measured. Quickness of foaming was evaluated by time required for the amount of foam to reach 250 mL.

The hair 1 used herein was 90 mm long, 30 g in weight in total, and attached onto a disk of approximately 160 mm in diameter. The container 10 was a cylinder of 160 mm in diameter and 20 mm high. The lid 20 had three first cylindrical projections 21 each having a diameter of 15 mm and a height of 12 mm, and nine second projections 22 each of which being 10 mm long, 2 mm wide, and 12 mm high. Number of rotations of the container 10 driven by the motor was set to 70 revolutions per minute.

Evaluation criteria are as follows:
⊚: shorter than 100 seconds;
○: 100 seconds or longer, shorter than 200 seconds;
Δ: 200 seconds or longer, shorter than 300 seconds; and
x: 300 seconds or longer.
(2) Anti-Dandruff Performance Ten male subjects were asked to wash their hair with each cleansing agent once a day for one month, then to stop washing for two days after the last washing. Hair of each subject was then washed twice using 3 g each of the same cleansing agent, and the whole volume of washate from the washing repeated twice was collected. The whole volume of collected washate was filtered through a 50 nylon mesh so as to remove unnecessary dust and hair. The whole volume of filtrate was filtered through a 255 nylon mesh (100×100 µm) preliminarily weighed, the nylon mesh was allowed to dry for approximately 48 hours at room temperature, and the amount of increase of weight thereof was determined as the weight of dandruff. Average values of weight of dandruff from ten subjects were determined, and evaluated according to the criteria below:
⊚: weight of dandruff≤30 mg;
○: 30 mg<weight of dandruff≤40 mg;
Δ: 40 mg<weight of dandruff≤50 mg; and
x: 50 mg<weight of dandruff.
(3) Swellability of the Horny Layer Human heel was disinfected with ethanol, the horny layer was scratched off, and then thoroughly dried to obtain a horny layer powder. Twenty milligrams of the thus-dried horny layer powder was placed in a 5-mm-diameter tube for NMR measurement, 0.8 mL of each hair cleansing agent diluted 20-fold with deionized water was injected thereinto, and the level of height of the mixture after being allowed to stand for 2 hours was measured. Evaluation was expressed by a relative value while assuming the level of height, attained when 0.8 mL of deionized water was added to 20 mg of the horny layer powder, as 100%. Larger value herein means larger level of swelling of the horny layer. Judgment criteria are as follows:
⊚: less than 110%;
○: 110% or more, less than 120%;
Δ: 120% or more, less than 125%; and
x: 125% or more.
(4) Anti-Itching Effect Ten male subjects were asked to use each cleansing agent and to wash their hair once a day for one month. After one month, itchiness of the scalp as washed was evaluated according to a scale of 1 to 5. The average of ten subjects of 4.0 or larger was rated "⊚", 3.2 to 3.9 was rated "○", 2.5 to 3.1 was rated "Δ", and 2.4 or smaller was rated "x":
5: itchiness decreased;
4: itchiness slightly decreased;
3: itchiness remained unchanged;
2: itchiness slightly increased; and
1: itchiness increased.

TABLE 1

| | | | Examples | | | | | | |
|---|---|---|---|---|---|---|---|---|---|
| | | | 1 | 2 | 3 | 4 | 5 | 6 | 7 |
| Composition | Component (A) | Ammonium polyoxyethylene (1) lauryl ether sulfate *1 | 11 | 8 | 13 | 11 | — | 11 | 11 |
| | | Sodium polyoxyethylene (Z) lauryl ether sulfate *2 | — | — | — | — | 11 | — | — |
| | Component (B) | Sodium polyoxyethylene (4.5) lauryl ether acetate *3 | 4 | 7 | 2 | — | 4 | 4 | 4 |
| | | Sodium polyoxyethylene (10) lauryl ether acetate *4 | — | — | — | 4 | — | — | — |
| | Comparative component (B') | Lauric acid | — | — | — | — | — | — | — |
| | | Sodium cocoylmethyl taurine | — | — | — | — | — | — | — |
| | Component (C) | Malic acid | 0.75 | 0.75 | 0.75 | 0.75 | 0.75 | 0.75 | 0.75 |
| | Other components | Dipotassium glycyrrhizinate | 0.1 | 0.1 | 0.1 | 0.1 | 0.1 | 0.1 | 0.1 |
| | | Lauroyl amidopropyl betaine | 1 | 1 | 1 | 1 | 1 | 1 | 1 |
| | | Monoisodecyl glyceryl ether | 2.5 | 2.5 | 2.5 | 2.5 | 2.5 | 2.5 | 2.5 |
| | | Ethylene glycol distearate | 2 | 2 | 2 | 2 | 2 | 2 | 2 |
| | | Cationized cellulose *5 | 0.5 | 0.5 | 0.5 | 0.5 | 0.5 | 0.5 | 0.5 |
| | | Glycerin | 0.5 | 0.5 | 0.5 | 0.5 | 0.5 | 0.5 | 0.5 |
| | | Polypropylene (7) glycol | 0.5 | 0.5 | 0.5 | 0.5 | 0.5 | 0.5 | 0.5 |
| | | Sodium Chloride | 0.3 | 0.3 | 0.3 | 0.3 | 0.3 | 0.3 | 0.3 |
| | | Potassium hydroxide *6 Purified water | proper quantity balance | proper quantity balance | proper quantity balance | proper quantity balance | proper quantity balance | proper quantity balance | proper quantity balance |
| | | Total | 100 | 100 | 100 | 100 | 100 | 100 | 100 |
| | | (B)/((B) + (A)) % by weight | 27 | 47 | 13 | 27 | 27 | 27 | 27 |
| | | pH | 3.7 | 3.7 | 3.7 | 3.7 | 3.7 | 3 | 4.5 |
| Results of evaluation | | Quickness of foaming (seconds) | ◎ (85) | ○ (110) | ◎ (70) | ○ (105) | ◎ (95) | ○ (102) | ◎ (80) |
| | | Anti-dandruff performance (weight of dandruff in mg) | ◎ (25) | ◎ (28) | ◎ (26) | ◎ (20) | ◎ (24) | ◎ (25) | ○ (35) |
| | | Swellability of horny layer (arbitrary value relative to water) | ◎ (108) | ◎ (105) | ○ (115) | ◎ (105) | ◎ (104) | ○ (110) | ◎ (106) |
| | | Anti-itching effect | ◎ | ◎ | ○ | ◎ | ◎ | ◎ | ◎ |

| | | | Comparative Examples | | | | | | | |
|---|---|---|---|---|---|---|---|---|---|---|
| | | | 1 | 2 | 3 | 4 | 5 | 6 | 7 | 8 |
| Composition | Component (A) | Ammonium polyoxyethylene (1) lauryl ether sulfate *1 | 15 | 11 | 11 | — | — | 11 | 11 | — |
| | | Sodium polyoxyethylene (Z) lauryl ether sulfate *2 | — | — | — | — | — | — | — | 11 |
| | Component (B) | Sodium polyoxyethylene (4.5) lauryl ether acetate *3 | — | — | — | 15 | — | 4 | — | 4 |
| | | Sodium polyoxyethylene (10) lauryl ether acetate *4 | — | — | — | — | 15 | — | 4 | — |
| | Comparative component (B') | Lauric acid | — | 4 | — | — | — | — | — | — |
| | | Sodium cocoylmethyl taurine | — | — | 4 | — | — | — | — | — |

TABLE 1-continued

|  |  |  |  |  |  |  |  |  |  |
|---|---|---|---|---|---|---|---|---|---|
| Component (C) | Malic acid | 0.75 | 0.75 | 0.75 | 0.75 | 0.75 | 0.1 | 0.1 | 0.1 |
| Other components | Dipotassium glycyrrhizinate | 0.1 | 0.1 | 0.1 | 0.1 | 0.1 | 0.1 | 0.1 | 0.1 |
|  | Lauroyl amidopropyl betaine | 1 | 1 | 1 | 1 | 1 | 1 | 1 | 1 |
|  | Monoisodecyl glyceryl ether | 2.5 | 2.5 | 2.5 | 2.5 | 2.5 | 2.5 | 2.5 | 2.5 |
|  | Ethylene glycol distearate | 2 | 2 | 2 | 2 | 2 | 2 | 2 | 2 |
|  | Cationized cellulose *5 | 0.5 | 0.5 | 0.5 | 0.5 | 0.5 | 0.5 | 0.5 | 0.5 |
|  | Glycerin | 0.5 | 0.5 | 0.5 | 0.5 | 0.5 | 0.5 | 0.5 | 0.5 |
|  | Polypropylene (7) glycol | 0.5 | 0.5 | 0.5 | 0.5 | 0.5 | 0.5 | 0.5 | 0.5 |
|  | Sodium Chloride | 0.3 | 0.3 | 0.3 | 0.3 | 0.3 | 0.3 | 0.3 | 0.3 |
|  | Potassium hydroxide *6 | proper quantity | proper quantity | proper quantity | proper quantity | proper quantity | proper quantity | proper quantity | proper quantity |
|  | Purified water | balance | balance | balance | balance | balance | balance | balance | balance |
|  | Total | 100 | 100 | 100 | 100 | 100 | 100 | 100 | 100 |
|  | (B)/((B) + (A)) % by weight | 0 | 27 | 27 | 100 | 100 | 27 | 27 | 27 |
|  | pH | 3.7 | 3.7 | 3.7 | 3.7 | 3.7 | 6 | 6 | 6 |
| Results of evaluation | Quickness of foaming (seconds) | ◉ (80) | ◯ (130) | ◯ (110) | △ (280) | X (310) | ◉ (90) | ◯ (110) | ◯ (105) |
|  | Anti-dandruff performance (weight of dandruff in mg) | ◯ (36) | ◯ (37) | ◯ (34) | ◯ (35) | △ (42) | X (55) | X (52) | X (52) |
|  | Swellability of horny layer (arbitrary value relative to water) | X (130) | X (125) | △ (122) | ◉ (105) | ◉ (100) | ◯ (119) | ◯ (115) | ◯ (115) |
|  | Anti-itching effect | X | △ | △ | ◯ | ◯ | △ | △ | △ |

*1 Ammonium polyoxyethylene (1) lauryl ether sulfate: $C_{12}:C_{14}$ = 75:25% by weight (Emal 125A from Kao Corporation, active component concentration = 25%)
*2 Sodium polyoxyethylene (2) lauryl ether sulfate: $C_{12}:C_{14}$ = 75:25% by weight (Emal 227 from Kao Corporation, active component concentration = 27%)
*3 Sodium polyoxyethylene (4.5) lauryl ether acetate: $C_{12}:C_{14}:C_{16}$ = 68:26:6% by weight (Kao-Akypo RLM-45NV from Kao Corporation, active component concentration = 23.5%)
*4 Sodium polyoxyethylene (10) lauryl ether acetate: $C_{12}:C_{14}:C_{16}$ = 68:26:6% by weight (Kao-Akypo RLM-100NV from Kao Corporation, active component concentration = 23.5%)
*5 Cationized cellulose: "POIZ ® C-80M" from Kao Corporation
*6 Potassium hydroxide was used as a pH adjusting agent.

It was found from Table 1 that the compositions of Examples 1 to 7 were excellent in foamability and anti-dandruff performance, highly effective in suppressing swelling of the horny layer, and effective in suppressing itchiness of the scalp.

|  | (% by weight) |
|---|---|
| Sodium polyoxyethylene (2) lauryl ether sulfate | 12.5 |
| Sodium polyoxyethylene (4.5) myristyl ether acetate | 2.5 |
| Lactic acid | 1.0 |
| Dipotassium glycyrrhizinate | 0.1 |
| Isodecyl glyceryl ether | 2.0 |
| Laurylhydroxy sulfobetaine | 1.0 |
| Cationized guar gum ("JAGUAR ® C-13", from Rhodia) | 0.2 |
| Cationized tara gum ("CATINAL ® CTR-100", from TOHO Chemical Industry Co., Ltd.) | 0.2 |
| Diallyl dimethyl ammonium chloride/acrylamide copolymer ("MERQUAT ® 550", from ONDEO Nalco Company, effective component = 8.5% by weight) | 1.2 |
| Dimethylpolysiloxane ("Silicone CF2450", from Dow Corning Toray Co., Ltd., effective component = 60% by weight) | 2.0 |
| Ethylene glycol distearate | 2.0 |
| Myristyl alcohol | 0.2 |
| Lauric acid | 0.1 |
| Polyoxyethylene (16) lauryl ether | 0.3 |
| Polypropylene glycol (weight average MW = 400) | 0.5 |
| Benzyl alcohol | 0.3 |

-continued

|  | (% by weight) |
|---|---|
| Ethanol | 3.0 |
| Camellia oil | 0.01 |
| Panthenol | 0.05 |
| Royal jelly | 0.01 |
| Purified honey | 0.01 |
| Silk extract | 0.05 |
| Sodium chloride | 0.2 |
| Perfume | proper quantity |
| pH adjusting agent (potassium hydroxide) | amount necessary for adjusting pH to 3.9 |
| Deionized water | balance |

|  | (% by weight) |
|---|---|
| Sodium polyoxyethylene (1) lauryl ether sulfate | 9.0 |
| Sodium polyoxyethylene (4.5) lauryl ether acetate | 6.0 |
| Glycolic acid | 2.0 |
| Dipotassium glycyrrhizinate | 0.1 |
| Coconut oil fatty acid monoethanolamide | 2.0 |
| Lauroylamidopropyl betaine | 2.5 |
| Cationized locust bean gum ("CATINAL ® CLB-100", from TOHO Chemical Industry Co., Ltd.) | 0.2 |
| Cationized fenugreek gum ("CATINAL ® CLB-100", from TOHO Chemical Industry Co., Ltd.) | 0.2 |

-continued

| | (% by weight) |
|---|---|
| Dimethylpolysiloxane ("Silicone CF2460", from Dow Corning Toray Co., Ltd., effective component = 75% by weight) | 3.0 |
| Aminopolyether-modified silicone ("Silicone SILSTYLE ® 104", from Dow Corning Toray Co., Ltd.) | 0.2 |
| Ethylene glycol distearate | 1.5 |
| Dipropylene glycol | 3.0 |
| Benzyloxy ethanol | 0.5 |
| 1-Menthol | 1.0 |
| Sodium chloride | 0.2 |
| Perfume | proper quantity |
| pH adjusting agent (potassium hydroxide) | amount necessary for adjusting pH to 3.5 |
| Deionized water | balance |

| | (% by weight) |
|---|---|
| Ammonium polyoxyethylene (1) lauryl ether sulfate | 12.0 |
| Sodium polyoxyethylene (4.5) lauryl acetate | 2.0 |
| Malic acid | 0.75 |
| Dipotassium glycyrrhizinate | 0.1 |
| Isodecyl glyceryl ether | 0.8 |
| Laurylhydroxy sulfobetaine | 1.7 |
| Cationized guar gum ("JAGUAR ® C-13S", from Rhodia) | 0.4 |
| Diallyl dimethyl ammonium chloride/acrylamide copolymer ("MERQUAT ® 550", from ONDEO Nalco Company, effective component = 8.5% by weight) | 1.9 |
| Dimethylpolysiloxane ("Silicone CF2450", Dow Corning Toray Silicone Co., Ltd., effective component = 60% by weight) | 0.5 |
| Ethylene glycol distearate | 2.0 |
| Lauric acid | 0.8 |
| Polypropylene glycol (weight average MW = 1000) | 1.0 |
| Benzyl alcohol | 0.3 |
| Ethanol | 3.0 |
| Purified honey | 0.01 |
| Shea butter | 0.01 |
| Glycylglycine | 0.05 |
| Perfume | proper quantity |
| pH adjusting agent (potassium hydroxide) | amount necessary for adjusting pH to 3.9 |
| Deionized water | balance |

The hair cleansing agents of Examples 8 to 10 were found to be excellent in foamability and anti-dandruff performance, and to have effects of suppressing swelling of the horny layer and itchiness of the scalp.

Example 11, Comparative Examples 9 and 10

In these Examples, suppressive performance of samples containing the component (A) against swelling of the horny layer was evaluated according to the method described below. Compositions and pH of the samples are listed in Table 2.
(Preparation of Surfactant Samples)
The components below were used as the surfactant.
Component (A): ammonium polyoxyethylene (1) lauryl ether sulfate
Component (B): sodium polyoxyethylene (4.5) lauryl ether acetate
Comparative Component (B'): Sodium Cocoyl Methyl Taurine In Example 11, malic acid and sodium hydroxide were used to adjust the pH of the sample to 3.7. On the other hand, in Comparative Example 9 and Comparative Example 10, malic acid and sodium hydroxide were used to adjust the pH of the sample to 6.0 or 3.7.
(Horny Layer Swellability Test)
Samples were measured according to (3) Swellability of the horny layer for Examples 1 to 7 and Comparative Examples 1 to 8, described in the above.

More specifically, the components (A) and (B) or (B') were added to deionized water, so as to adjust the surfactant concentration, or the total concentration of the components (A) and (B) or (B'), to 30 mM, to thereby prepare surfactant samples having various concentrations as listed in Table 2. The surfactant concentration herein corresponds to a concentration of the shampoo when foamed on hair during washing.

On the other hand, 20 mg of the horny layer powder was placed into the NMR measurement tube, and 0.8 mL of each of the above-described surfactant samples was added and mixed.

Figure 2:
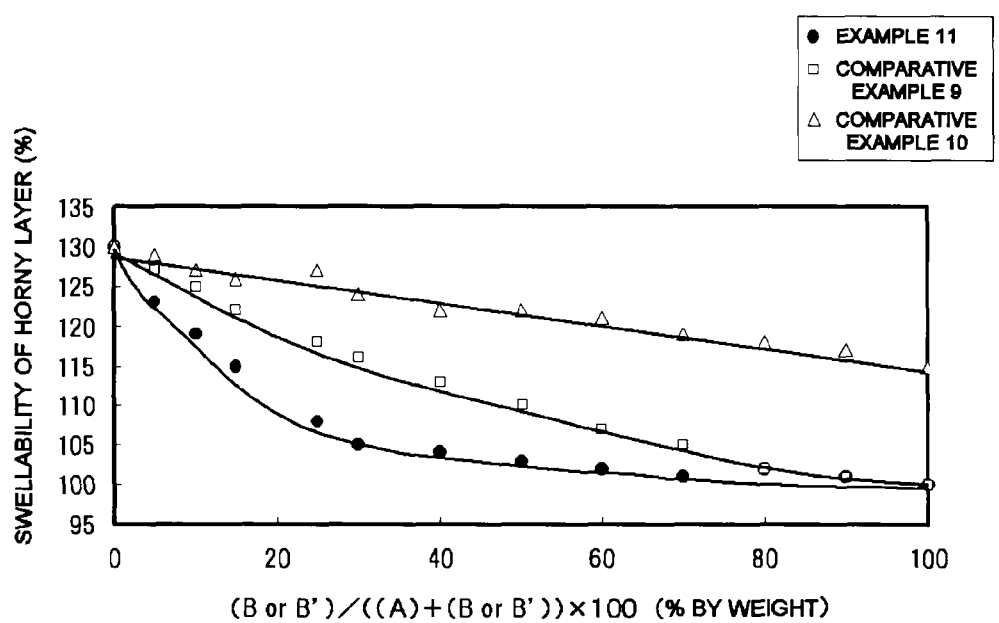
FIG. 2 is a drawing illustrating results of measurement of swellability of the horny layer in Examples.

Following addition of each surfactant sample, the level of height of the horny layer after being allowed to stand for two hours was measured. Results are shown in FIG. 2. In FIG. 2, "swellability of the horny layer" on the ordinate is given by relative values of the level of height of the horny layer swelled with the individual samples, while assuming the level of height, attained when 0.8 mL of deionized water, in place of the surfactant samples, was added to 20 mg of the horny layer powder and allowed to stand for two hours, as 100%. Larger value herein means larger level of swelling of the horny layer.

TABLE 2

| | Component (A) | Component (B or B') | pH | (B or B')/((A) + (B or B') % by weight | | | | | | | | | | | | |
|---|---|---|---|---|---|---|---|---|---|---|---|---|---|---|---|---|
| | | | | 0 | 5 | 10 | 15 | 25 | 30 | 40 | 50 | 60 | 70 | 80 | 90 | 100 |
| Example 11 | Ammonium polyoxyethylene (1) lauryl ether sulfate | Sodium polyoxyethylene (4.5) lauryl ether acetate | 3.7 | 130 | 123 | 119 | 115 | 108 | 105 | 104 | 103 | 102 | 101 | 102 | 101 | 100 |
| Comparative Example 9 | Ammonium polyoxyethylene (1) lauryl ether sulfate | Sodium polyoxyethylene (4.5) lauryl ether acetate | 6.0 | 130 | 127 | 125 | 122 | 118 | 116 | 113 | 110 | 107 | 105 | 102 | 101 | 100 |
| Comparative Example 10 | Ammonium polyoxyethylene (1) lauryl ether sulfate | Sodium cocoylmethyl taurine | 3.7 | 130 | 129 | 127 | 126 | 127 | 124 | 122 | 122 | 121 | 119 | 118 | 117 | 115 |

It was found from FIG. 2 that Example 11 was capable of further effectively suppressing swelling of the horny layer, only with a small amount of addition, by using the component (A) together with the component (B), still also with the component (C), and by lowering the pH. Also Comparative Example 9, with its pH adjusted to 6.0, was found to be more effective in suppressing swelling of the horny layer, as compared with Comparative Example 10 having no component (B) contained therein. Example 11 showed a more distinctive effect of suppressing swelling of the horny layer. Example 11 was found to be excellent, also in terms of more stably obtaining a sample well balanced between the swellability and foamability.

This application claims priority right based on Japanese Patent Application No. 2009-085836 filed on Mar. 31, 2009, the entire content of which is incorporated hereinto by reference.

The present invention also includes the embodiments described below:

[1] An aqueous hair cleansing agent which includes components (A) and (B):

(A) a sulfate-type anionic surfactant represented by the following general formula (1):

$$R^1O(CH_2CH_2O)_nSO_3M \quad (1)$$

(in the general formula (1), $R^1$ represents an alkyl group or alkenyl group having 10 to 18 carbon atoms, M represents a cation derived from alkali metal, alkali earth metal, ammonium, alkanolamine or basic amino acid, and n represents a number from 0 to 5 estimated based on weight average); and (B) an ether carboxylate-type anionic surfactant represented by the following general formula (2) or (3):

$$R^2O(CH_2CH_2O)_mCH_2COOX \quad (2)$$

$$R^2C(=O)NH(CH_2CH_2O)_mCH_2COOX \quad (3)$$

(in the general formulae (2) and (3), $R^2$ represents an alkyl group or alkenyl group having 10 to 18 carbon atoms, X represents a cation derived from alkali metal, alkali earth metal, ammonium, alkanolamine or basic amino acid, and m represents a number of 0.5 to 10 estimated based on weight average.), and further including water, the aqueous hair cleansing agent having a pH of 1 to 5 at 25° C. when diluted 20-fold with water;

[2] The aqueous hair cleansing agent described in [1], further containing component (C) an organic carboxylic acid or salt thereof;

[3] The aqueous hair cleansing agent described in [1] or [2], wherein ratio of the component (B), relative to the total of the components (A) and (B), is 50% or less based on the weight ratio; and

[4] The aqueous hair cleansing agent described in any one of [1] to [3], further containing at least one species of anti-inflammatory agent in an amount of from 0.001 to 10% by weight.

The invention claimed is:

1. An aqueous hair cleansing agent
(1) comprising components (A), (B) and (C):
(A) sulfate anionic surfactant represented by the formula (1):

$$R^1O(CH_2CH_2O)_nSO_3M \quad (1),$$

wherein $R^1$ represents an alkyl group or alkenyl group having from 10 to 18 carbon atoms, M represents a cation derived from an alkali metal, an alkali earth metal, ammonium, alkanolamine or a basic amino acid, and n represents a number from 0 to 5 estimated based on the weight average, and wherein the content of the component (A) is from 1 to 25% by weight of the total aqueous hair cleansing agent;

(B) an ether carboxylate anionic surfactant represented by the formula (2) or (3):

$$R^2O(CH_2CH_2O)_mCH_2COOX \quad (2)$$

$$R^2C(=O)NH(CH_2CH_2O)_mCH_2COOX \quad (3),$$

wherein $R^2$ represents an alkyl group having from 12 to 16 carbon atoms, X represents a cation derived from an alkali metal, an alkali earth metal, ammonium, alkanolamine or a basic amino acid, and m represents a number of 0.5 to 10 estimated based on weight average, wherein the content of the component (B) is from 0.5 to 10% by weight of the total aqueous hair cleansing agent;

(C) an organic carboxylic acid or a salt thereof, wherein the content of the (C) organic carboxylic acid or salt thereof is from 0.1 to 5% by weight of the total aqueous hair cleansing agent, wherein the organic carboxylic acid (C) is at least one acid selected from the group consisted of glycolic acid, lactic acid, malonic acid, maleic acid, and malic acid; and water, and (2) having a pH of from 1 to 5 at 25° C. when diluted 20-fold with water.

2. The aqueous hair cleansing agent according to claim 1, wherein a ratio of the component (B), relative to the total of the components (A) and (B), is 50% or less based on the weight ratio.

3. The aqueous hair cleansing agent according to claim 1, further comprising at least one anti-inflammatory agent in an amount of from 0.001 to 10% by weight.

4. A method for cleansing hair, comprising applying the aqueous hair cleansing agent according to claim 1 to hair.

5. The aqueous hair cleansing agent according to claim 3, wherein the anti-inflammatory agent is at least one agent selected from the group consisting of glycyrrhetinic acid, glycyrrhizic acid, ε-aminocaproic acid, allantoin, sodium guaiazulene sulfonate, d-camphor, l-menthol, urea, pyridoxine dipalmitate, glycyrrhetinyl stearate, tranexamic acid, vitamin A oil, hydrocortisone, prednisolone, pyridoxine hydrochloride, zinc oxide, and hydrocortisone acetate.

6. The aqueous hair cleansing agent according to claim 3, wherein the anti-inflammatory agent is at least one salt of glycyrrhetinic acid or glycyrrhizic acid selected from the group consisting of a sodium salt, potassium salt, and ammonium salt.

7. The aqueous hair cleansing agent according to claim 3, wherein the anti-inflammatory agent is at least one salt selected from the group consisting of dipotassium glycyrrhizinate, disodium glycyrrhizinate, trisodium glycyrrhizinate, monoammonium glycyrrhizinate, glycerin glycyrrhetinate, and stearyl glycyrrhetinate.

8. The aqueous hair cleansing agent according to claim 3, wherein the anti-inflammatory agent is at least one salt selected from the group consisting of disodium glycyrrhizinate, trisodium glycyrrhizinate, monoammonium glycyrrhizinate, glycerin glycyrrhetinate, and stearyl glycyrrhetinate.

9. The aqueous hair cleansing agent according to claim 3, wherein the anti-inflammatory agent is at least one ester of glycyrrhetinic acid or glycyrrhizic acid selected from the group consisting of glycerin ester and stearyl ester.

10. The aqueous hair cleansing agent according to claim 3, wherein the amount of the anti-inflammatory agent is from 0.01 to 1% by weight.

* * * * *